United States Patent [19]

Shikata et al.

[11] 4,217,298

[45] Aug. 12, 1980

[54] PROCESS FOR PREPARING ORGANIC CARBONATES

[75] Inventors: Kazuo Shikata, Tokuyama; Toshiaki Shigemune, Hohfu, both of Japan

[73] Assignee: Tokuyama Soda Kabushiki Kaisha, Japan

[21] Appl. No.: 938,921

[22] Filed: Sep. 1, 1978

[30] Foreign Application Priority Data

Sep. 5, 1977 [JP] Japan ................................ 52-105897
Dec. 21, 1977 [JP] Japan ................................ 52-152836

[51] Int. Cl.$^2$ ............................................ C07C 68/04
[52] U.S. Cl. ................................................... 260/463
[58] Field of Search ........................................ 260/463

[56] References Cited

U.S. PATENT DOCUMENTS

| 2,648,678 | 8/1953 | Heiberger | 260/463 |
| 2,648,697 | 8/1953 | Heiberger | 260/463 |
| 2,784,201 | 3/1957 | Chitwood | 260/463 |
| 2,983,749 | 5/1961 | Shepherd | 260/463 |
| 3,657,310 | 4/1972 | Frevel | 260/463 |
| 4,009,183 | 2/1977 | Fumagalli et al. | 260/340.2 |
| 4,116,997 | 9/1978 | Cipriani et al. | 260/463 |

FOREIGN PATENT DOCUMENTS

| 46-09686 | 3/1971 | Japan | 260/463 |
| 666560 | 2/1952 | United Kingdom | 260/463 |

OTHER PUBLICATIONS

K. Soga et al., Makromol. Chem., 178, 2747-2751 (1977), A Convenient Synthesis of a Polycarbonate.

Primary Examiner—Glennon H. Hollrah
Assistant Examiner—M. C. Eakin
Attorney, Agent, or Firm—Wenderoth, Lind & Ponack

[57] ABSTRACT

A process for producing an organic carbonate, which comprises reacting an alkali metal carbonate, carbon dioxide gas, an alcohol and an organic halide in the presence of a catalyst.

12 Claims, No Drawings

PROCESS FOR PREPARING ORGANIC CARBONATES

This invention relates to a process for preparing organic carbonates with good selectivity and in good yields by a novel reaction procedure. It relates to a novel process for synthesizing organic carbonates which can afford asymmetric organic carbonates or symmetric organic carbonates with good selectivity mainly by specific selection and combination of starting alcohols and organic halogen compounds.

More specifically, the invention relates to a process for preparing organic carbonates which comprises reacting alkali metal carbonates, carbon dioxide gas, alcohols and organic halides in the presence of catalysts.

It is known that organic carbonates are used as plasticizers, additives, lubricants, solvents, etc. It is also known that organic carbonates having unsaturated bonds are used as raw materials for polymers, and polymers prepared from them are used as eyeglass lenses, windwhields of helicopters, etc. Various methods have been known to synthesize organic carbonates, and some examples are given below.

(1) Reaction of an alcohol with phosgene $$2R'OH + COCl_2 \rightarrow R'OCO_2R' + 2HCl$$

(R' = alkyl)

(2) Reaction of an alcohol with phosgene followed by reacting the product with another alcohol $$R'OH + COCl_2 \rightarrow ClCO_2R' + HCl$$

$$ClCO_2R' + R''OH \rightarrow R''OCO_2R' + HCl$$

(R', R'' = alkyl)

(3) Reaction of silver carbonate with an alkyl iodide $$Ag_2CO_3 + 2R'I \rightarrow R'OCO_2R' + 2AgI$$

(R' = alkyl)

(4) Reaction of an aralkyl chloride with sodium carbonate in the presence of a catalyst $$2ArCH_2Cl + Na_2CO_3 \rightarrow (ArCH_2O)_2CO + 2NaCl$$

(Ar = substituted or unsubstituted aromatic group)

(5) Reaction of allyl chloride with sodium carbonate in the presence of a catalyst

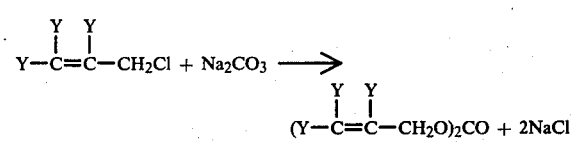

(Y = H, Cl or CH₃)

In methods (1) and (2), handling of phosgene is inconvenient because it is strongly poisonous. Moreover, these methods have the defect that a neutralizing agent is required to neutralize the by-product HCl. Method (3) is not economical because of the high cost of the starting silver carbonate, and cannot produce asymmetric organic carbonates with good selectivity. Methods (4) and (5) involve very restricted reactions, and cannot give asymmetric organic carbonates with good selectivity.

The present inventors made extensive investigations about a process for producing organic carbonates which would be free from the aforesaid defects.

These investigations led to the discovery that both asymmetric and symmetric organic carbonates can be produced with high selectivity and in high yields by a novel reaction procedure which can be applied to the production of a broad range or organic carbonates from non-toxic readily available raw materials with operational and economic advantages.

The investigations of the present inventors show that organic carbonates can be easily prepared with the aforesaid advantages by reacting an alkali metal carbonate, carbon dioxide gas, an alcohol and an organic halide in the presence of a catalyst, and that the reaction can be advantageously carried out in one step although it may be performed in two steps as required.

It is an object of this invention therefore to provide a process for producing organic carbonates with the aforesaid advantages by a novel reaction procedure.

The above and other objects and advantages of the invention will become more apparent from the following description.

According to this invention, an alkali metal carbonate, carbon dioxide gas, an alcohol and an organic halide are reacted in the presence of a catalyst.

Examples of preferred alkali metal carbonates are normal carbonates such as sodium carbonate and potassium carbonate and bicarbonates such as sodium bicarbonate and potassium bicarbonate. Of these, the normal carbonates are preferred, and the use of sodium carbonate is especially preferred from the viewpoint of its cost. As the sodium carbonate, light soda ash obtained by calcining sodium bicarbonate crystals is preferable to dense soda ash, because it does not require a pulverizing operation and has good reactivity, the by-product salt after the reaction can be easily separated by filtration, and it is expected to bring about an effect of increasing the selectivity and yield of the desired organic carbonates. Since the type of the alkali metal salt used can vary according to the types of the alcohol and the organic halide, the reaction conditions, etc., it should be experimentally selected and determined in advance according to these factors.

The alcohol, another starting material used in the process of this invention, may be any alcohol having an alcoholic hydroxyl group. Examples of suitable alcohols are those of the formula

R—OH wherein R represents a moiety selected from the group consisting of saturated or unsaturated alkyl groups optionally substituted by at least one member of the group consisting of a hydroxyl group, alkoxy groups and hydroxyalkoxy groups; and aralkyl groups optionally substituted by at least one member of the group consisting of a hydroxyl group and alkoxy groups.

The saturated alkyl groups may contain 1 to 15 carbon atoms, preferably 1 to 12 carbon atoms. The unsaturated alkyl groups may contain 2 to 15 carbon atoms, preferably 2 to 12 carbon atoms. The alkoxy groups may be those having 1 to 10 carbon atoms, preferably 1 to 6 carbon atoms. Alcohols having a hydroxyalkoxy group include polyalkylene glycols formed by the repetitive ether linkage of an alkylene group. The hydroxyalkoxy group has 1 to 60, preferably 1 to 50, carbon atoms. Examples of the aralkyl groups are those having 7 to 15 carbon atoms, preferably 7 to 11 carbon atoms. Preferred alcohols for use in this invention are the polyalkylene glycols, and lower alcohols having 1 to 15 carbon atoms which may contain a substituent, in view of their availability, handling, purification, etc.

Specific examples of such alcohols include primary alcohols such as methanol, ethanol, propanol, butanol, iso-butanol, allyl alcohol, methallyl alcohol and normal dodecyl alcohol; secondary alcohols such as iso-propanol and sec-butanol; tertiary alcohols such as tert-butanol; polyhydric alcohols such as ethylene glycol, propylene glycol, 1,3-propanediol, 1,4-butanediol, 2-butene-1,4-diol, diethylene glycol, triethylene glycol, dipropylene glycol and glycerol; and aralkyl alcohols such as benzyl alcohol, phenethyl alcohol and xylylene glycol. Polyalkylene glycols such as polyethylene glycol or polypropylene glycol and alkoxy alcohols such as Cellosolve (Trademark of Union Carbide Corporation) and Carbitol (Trademark of Union Carbide Corporation) can also be used. Preferred polyalkylene glycols have an average molecular weight of about 100 to about 1,000.

The organic halide, another starting material used in the process of this invention, may be any compounds having a reactive halogen group. Examples of preferred organic halides are those of the following formula

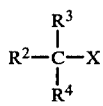

wherein $R^2$, $R^3$ and $R^4$, independently from each other, represent a moiety selected from the group consisting of a hydrogen atom; saturated or unsaturated alkyl groups optionally substituted by at least one member of the group consisting of alkoxy groups and halogen atoms; a phenyl group optionally substituted by at least one member of the group consisting of alkyl groups, a vinyl group, a phenyl group, alkoxy groups and halogen atoms; and aralkyl groups optionally substituted by at least one member of the group consisting of alkoxy groups and halogen atoms; and X represents a halogen atom.

Preferred alkoxy groups as substituents have 1 to 6 carbon atoms, preferably 1 to 4 carbon atoms. Preferred halogen atoms as substituents are chlorine, bromine and iodine. Preferred saturated alkyl groups have 1 to 15 carbon atoms, preferably 1 to 12 carbon atoms. Preferred unsaturated alkyl groups have 2 to 15 carbon atoms, preferably 2 to 12 carbon atoms.

The substituent alkyl group which the phenyl group may have is preferably an alkyl group with 1 to 6 carbon atoms, more preferably an alkyl group with 1 to 4 carbon atoms. Preferred aralkyl groups include those having 7 to 15 carbon atoms, preferably 7 to 11 carbon atoms. Preferred X's are Cl, Br and I.

Specific examples of the organic halide thus include methyl chloride, ethyl chloride, propyl chloride, iso-propyl chloride, butyl chloride, sec-butyl chloride, iso-butyl chloride, tert-butyl chloride, allyl chloride, methallyl chloride, chloroprene, benzyl chloride, methylbenzyl chloride, chloromethylstyrene, ethylene dichloride, 1,3-dichloropropane, 1,4-dichlorobutane, 1,4-dichloro-2-butene, dichloroethyl ether, and xylylene dichloride. Above all, compounds having a halogen group at the allyl position or the benzyl position have superior reactivity, and are used conveniently. Bromides and iodides corresponding to the above-exemplified chlorides can be equally used.

Especially preferred organic halides are allyl or methallyl halides such as allyl chloride and methallyl chloride, benzyl halide and derivatives thereof. Examples of such benzyl halide and its derivatives are compounds of the following formula

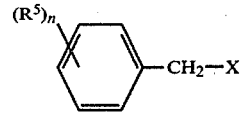

wherein $R^5$ represents a member selected from the group consisting of the aforesaid alkyl groups, vinyl group, phenyl group, alkoxy groups and halogen atoms, X represents a halogen atom, and n is a positive integer of 0 to 5, and when n is other than 0, $R^5$ groups groups may be the same or different.

Any carbon dioxide gas irrespective of the method of its production can be used in this invention. Generally, it is used alone, but may be used as the admixture with a gas which is inert under the reaction conditions, such as nitrogen, argon, neon, helium, and hydrogen. When carbon dioxide gas is used as a mixture with an inert gas, it is economical to minimize the total pressure of the reaction system. Generally, therefore, it is preferred that the gaseous portion of the reaction system should contain at least 50%, preferably at least 90%, of carbon dioxide gas. Liquefied carbon dioxide gas generally sold on the market has a purity of more than 99%, and can be conveniently used as a source of carbon dioxide gas in the process of the invention.

According to the process of the invention, the alkali metal carbonate, carbon dioxide gas, alcohol and organic halide described hereinabove are reacted in the presence of a catalyst. Quaternary salts of nitrogen or phosphorus can, for example, be used as the catalyst. Compounds which react with the organic halide in the reaction system to yield such a quaternary salt can also be used as the catalyst. For example, catalysts selected from tertiary amine compounds, quaternary ammonium compounds, phosphines and crown ethers can be used. Of these, the tertiary amine compounds and/or quaternary ammonium compounds are more preferred.

Examples of the tertiary amine compounds and quaternary ammonium compounds are compounds of the following formulae:

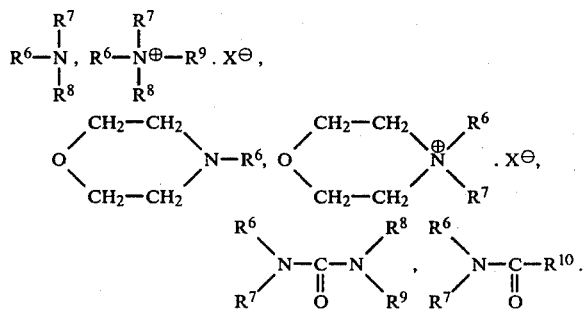

In the above formulae, $R^6$, $R^7$, $R^8$ and $R^9$, independently from each other, represent a moiety selected from the group consisting of saturated or unsaturated alkyl groups, preferably saturated alkyl groups with 1 to 6 carbon atoms, more preferably saturated alkyl groups with 1 to 4 carbon atoms, preferably unsaturated alkyl groups with 2 to 6 carbon atoms, more preferably unsaturated alkyl groups with 2 to 4 carbon atoms; cycloalkyl groups, preferably cycloalkyl groups with 3 to 7 carbon atoms, more preferably cycloalkyl groups with 4 to 6 carbon atoms; aromatic hydrocarbon groups, preferably aromatic hydrocarbon groups with 6 to 11 carbon atoms, more preferably aromatic hydrocarbon groups with 6 to 8 carbon atoms; and aralkyl groups, preferably aralkyl groups with 7 to 12 carbon atoms, more preferably 7 to 9 carbon atoms. $R^{10}$ represents a moiety selected from the same groups as given above for $R^6$, $R^7$, $R^8$ and $R^9$, and a hydrogen atom. $X^\ominus$ represents a monovalent anion, preferably an anion selected from the group consisting of $Cl^-$, $Br^-$, $I^-$ and $OH^-$.

Examples of the phosphines are compounds of the following formulae:

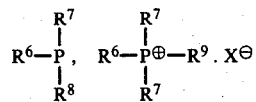

In these formulae, $R^6$, $R^7$, $R^8$, $R^9$ and $X^\ominus$ are same as defined hereinabove.

Specific examples of the catalyst compounds described above include trimethylamine, triethylamine, tri-n-propylamine, diethylbutylamine, N,N-dimethylbenzylamine, N,N-dimethylaniline, tetraethyl ammonium bromide, allyl triethyl ammonium chloride, dimethyl formamide, dimethyl acetamide, trimethyl phosphine, triethyl phosphine and dibenzo-18-crown-6.

The novel reaction procedure used in the process of this invention can be schematically shown as follows (taking up an example of using R—OH):

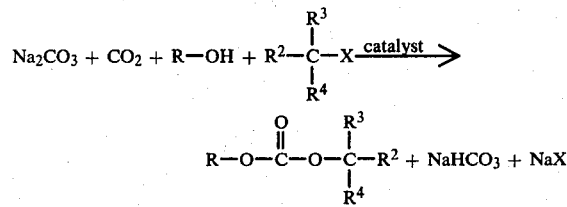

The present inventors theorize that the reaction proceeds consecutively as shown by the following two reaction formulae.

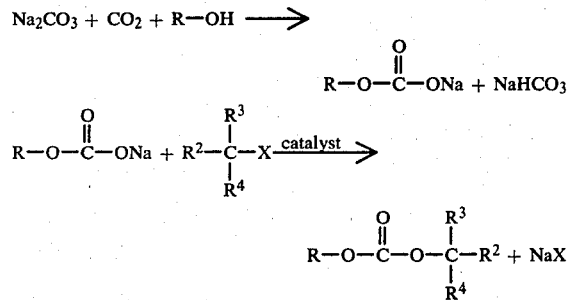

It should be noted however that the present invention is in no way restricted by this theory.

When ay one of $R^2$, $R^3$ and $R^4$ of the organic carbonate of the formula

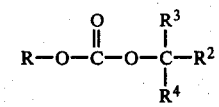

in the aforesaid moiety substituted with halogen and the substitution position of the halogen is the one which has high reactivity, the resulting organic carbonate participates in the above reaction as the organic halide, and an organic carbonate having a plurality of carbonate groups such as expressed by the following formula can be formed.

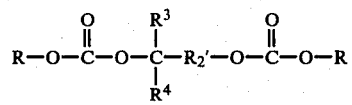

(wherein $R'_2$ is the same as $R^2$, $R^3$ or $R^4$ in the formula

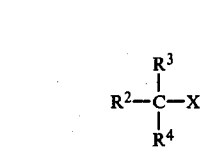

given hereinabove except that the substituent is not a halogen atom) When R in R-OH is a moiety substituted by an alcohol group, an organic carbonate having two carbonate groups in the molecule, such as the one expressed by the following formula,

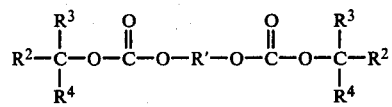

(wherein R' is the same as R in the formula R—OH given hereinabove except that the substituent is not a hydroxyl group) will be formed.

The process of the invention can be performed either by one step or by two steps.

For example, an organic carbonate can be formed in one step by feeding the alkali metal carbonate, carbon dioxide gas, alcohol and organic halide into a reaction zone, and reacting them in the presence of a catalyst at a temperature of, for example, about 70° to about 150° C., preferably about 80° to about 120° C. In an alternative embodiment, the above one-step process is carried out at room temperature to about 70° C. in the early stage, and at about 70° to 150° C. at the intermediate to the last stage. Elevation of the reaction temperature may be performed progressively or stepwise, for example.

Or an organic carbonate can be formed by a two-step process consisting of a first step in which the alkali metal carbonate, carbon dioxide gas and alcohol are fed into a reaction zone and reacted in accordance with the first reaction formula shown hereinabove, and a second step in which

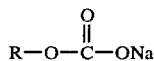

is separated from the reaction mixture and reacted in the presence of the organic halide and catalyst. According to another embodiment, the separation of the product from the reaction mixture is omitted, and the reaction according to the second formula shown hereinabove is performed by adding the organic halide and catalyst to the reaction mixture obtained in the first stage. In the performance of the two-step process, the first step is should preferably be carried out at room temperature to about 70° C., and the second step, at a temperature of more than 70° C. and up to about 150°, more preferably from about 80° to about 120° C.

In the performance of the one-step process, the reaction of the alkali metal carbonate, carbon dioxide gas and alcohol proceeds at sufficiently high speeds even at room temperature. Hence, the formation of an intermediate of the formula

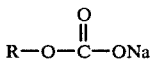

can be effected sufficiently within a time during which the temperature is elevated to a reaction temperature of about 70° to about 150° C. Accordingly, in the performance of the one-step process, it is preferred to charge the starting componds at room temperature, elevating the temperature to the desired reaction temperature, and react these compounds at the temperature attained. Preferably, the reaction is carried out in the presence of a solvent. The organic halide itself may be used concurrently as a solvent. Nitriles and N-substituted amides can also be used as the solvent.

In the performance of the two-step process, the first step is completed in several minutes to several tens of minutes. The reaction product formed by the first step is then reacted with the organic halide in the presence of a catalyst in the second step. At this time, the intermediate

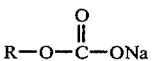

may be separated and reacted in the second step, or the reaction mixture may be directly reacted in the second step.

In the two-step process, the first step is preferably carried out by successively adding the alcohol to an inert solvent containing the alkali metal carbonate and carbon dioxide gas to prevent the hardening of the carbonate salt. Hydrocarbons, ethers, esters and ketones as well as the aforesaid nitriles and N-substituted amides can be used as the inert solvent. The successive addition can be effected by adding the alcohol in small portions either continuously or intermittently. Preferably, the second step is carried out in an atmosphere of carbon dioxide gas.

In the two-step process, the first-step reaction and the second-step reaction are carried out preferably in a solvent. For the second-step reaction, the same solvents as described above with regard to the one-step process, such as the organic halides, nitriles and N-substituted amides, may be used. As the reaction solvent for the first-step reaction, various other compounds which are inert under the reaction conditions of the first step can be used since the first-step reaction is carried out at a temperature of as low as about 70° C. or lower. Usually, the organic halide, which in a starting material, is most suitably used as a solvent in the second-step reaction. It is also possible to use those compounds which are inert under the reaction conditions and are selected from hydrocarbons, ethers, esters, ketones, nitriles and N-substituted amides. Specific examples of solvents which can be used in the first-step reaction include hexane, heptane, cyclohexane, benzene, toluene, dichloromethane, chloroform, carbon tetrachloride, 1,2-dichloroethane, 1,1,1-trichloroethane, trichloroethylene, tetrachloroethylene, 1,2-dichloropropane, allyl chloride, butyl chloride, chlorobenzene, ethyl ether, isopropyl ether, dioxane, tetrahydrofuran, diethylene glycol dimethyl ether, acetone, methyl ethyl ketone, methyl isobutyl ketone, methyl acetate, ethyl acetate, diethyl carbonate, propylene carbonate, acetonitrile, propionitrile, N,N-dimethyl formamide, and dimethyl sulfoxide.

In the performance of the process of this invention, the reaction is preferably carried out in the substantial absence of water. Desirably, therefore, the starting compounds, especially the alcohol and the organic halide, and the reaction solvent should be dehydrated to a substantially anhydrous state prior to use. It is desired to avoid the presence of a substantial amount of water in the reaction system because it will facilitate the formation of a by-product ether compound. Furthermore, the alkali metal carbonate as one starting compound may conveniently be added to the reaction system in excessive amounts so as to make it act concurrently as a dehydrating agent.

The use of a reaction solvent is preferred in the practice of the process of this invention. The alcohol and the organic halide as starting materials may be used in excess to make them serve also as a solvent. The use of an inert organic solvent is also suitable. Any inert organic solvents can be used which are inert under the reaction conditions. Nitriles and N-substituted amides are especially preferred. Specifically, acetonitrile, propionitrile, N,N-dimethyl formamide, and N,N-dimethyl acetamide are most suitable in inert organic solvents.

The amount of each of the starting materials varies according to its type, the reaction conditions, etc, and is difficult to determine definitely. Furthermore, since the starting material is used preferably in an amount which makes it serve also as a solvent when an inert organic solvent is not particularly used, the amount of the starting material naturally differs from the case of using a solvent in the reaction system. Accordingly, it is desirable that a suitable amount of each starting material should be determined according to the type of each material, the reaction conditions, etc.

As stated hereinabove, the organic halide, one starting material, can be made to serve concurrently as a solvent. When an inert solvent is used in the reaction system, the organic halide may be used in an amount equal to, or more than, the equivalent mole usually required for the reaction. Generally, to expect its action as a solvent, the organic halide is used in an amount of 1.2 to to 10 moles per mole of the hydroxyl group of the alcohol.

When the amount of the alkali metal carbonate, another starting material, is insufficient, the amount of a by-product ether tends to increase. If the amount is too large, the amount of the by-product increases and at the same time, the separation of the unreacted alkali metal carbonate is adversely affected. From the commercial standpoint, the suitable amount of the alkali metal carbonate is at least 1 mole, for example 1 to about 2 moles, preferably from about 1.05 to about 1.5 moles, per mole of the hydroxyl group of the alcohol.

Carbon dioxide gas is another starting material, and also serves to inhibit the formation of the by-product ether. Preferably, it is used in an amount more than the required mole equivalent. Generally, the suitable amount of carbon dioxide is such that the partial pressure of carbon dioxide in the reaction system at the time of feeding the starting materials (namely, before the elevation of temperature) is at least 0.5 kg/cm$^2$, preferably at least 1 kg/cm$^2$, more preferably at least 2 kg/cm$^2$. The higher the partial pressure of carbon dioxide is, the better is the selectivity of the organic carbonate. When the partial pressure is raised to a certain point, the effect does not further increase, and for higher partial pressures, the reaction apparatus must have resistance to such pressures. Generally, it is economically convenient that the partial pressure of carbon dioxide at the time of feeding the starting materials is adjusted to not more than 50 kg/cm$^2$, preferably not more than 20 kg/cm$^2$.

The reaction can be performed either batchwise, semi-batchwise, or continuously both in the one-step process and the two-step process. When the two-step process is employed, it can be performed continuously by carrying out the first-step reaction and the second-step reaction industrially in separate reaction tanks. A continuous reaction is of course possible in the one-step process. However, when a continuous method is used in the one-step process, the amount of the by-product ether tends to increase depending upon the types of the starting materials, the reaction conditions, etc. It is desirable therefore to check the types of the starting materials and the reaction conditions prior to performing the reaction.

The process of this invention can be performed by a one-step process or a two-step process. In any of these processes, the reaction is preferably carried out in an atmosphere of carbon dioxide gas. The reaction pressure differs according to the reaction temperature. Generally, the pressure at the time of charging the starting materials (namely, before the elevation of the temperature) is within the range of 10 to 50 kg/cm$^2$.

The following Examples are given to illustrate the present invention more specifically. It should be understood that the invention is not limited to these Examples.

The alcohols used in these Examples were refluxed after the addition of anhydrous magnesium sulfate, and then distilled prior to use. The organic halides used in these Examples were dried with anhydrous calcium chloride and distilled prior to use.

Sodium carbonate and potassium carbonate were obtained by pulverizing anhydrous reagent grades by a porcelain ball mill, and vacuum-drying them at 100° C.

Light soda ash was obtained by vacuum-drying a commercial grade light soda ash at 100° C.

Sodium hydrogen carbonate used was of a reagent grade.

The "neutralization ratio" shown in the Examples denotes the ratio of the alkali metal chloride converted from the alkali metal carbonate. It was obtained by determining the amount of halogen in the solid which remained after the reaction by the method to be described below.

The solid in the reaction mixture was recovered by filtration. It was fully washed with ethanol, and vacuum-dried overnight at 60° C. About 0.6 g of the solid was formed into 100 cc of an aqueous solution. The solution was titrated using a silver nitrate solution as a standard solution and an aqueous solution of potassium chromate as an indicator.

The "selectivities" were determined by analysis of the reaction mixture by gas-chromatography. The selectivity of a particular product is expressed as the proportion of the peak area of the product based on the entire peak area excepting the peaks of the alcohol and the organic halide and of the solvent if used. For convenience, a value obtained by multiplying the peak height by a half value width was used as the peak area.

Gas-chromatography (G.C.) was carried out with the aid of model GC-6A (a device of Shimadzu Seisakusho). The column used had a length of 3 m and Silicone SE-30 (a trademark for a product of Gaschro Kogyo Kabushiki Kaisha) was used as a filler. Hydrogen was used as a carrier gas.

EXAMPLES 1 to 3

A 500 cc autoclave (made of SUS 136 stainless steel of JIS) equipped with a stirrer was charged with 46 g (1 mole) of ethanol, 77 g (1 mole) of allyl chloride, 3.2 g of triethylamine, and each of the alkali metal carbonates shown in Table 1 in the amounts indicated. The autoclave was purged with carbon dioxide gas, and with stirring at 1000 rpm, the reaction system was pressurized with carbon dioxide gas to 10 kg/cm$^2$.G at room temperature. The temperature was raised to 120° C. over the course of about 20 minutes.

These starting materials were reacted at 120° C. for 4 hours. The reaction product was separated by filtration. The organic layer was analyzed by gas chromatography, and the remaining salt was titrated. The results are shown in Table 1.

Table 1

| Example | Alkali metal carbonate Type | Amount [g(M)] | Neutralization ratio (%) | Selectivities (%) Allyl ethyl carbonate | Allyl ethyl ether | Diallyl carbonate |
|---|---|---|---|---|---|---|
| 1 | Sodium carbonate | 53 (0.5) | 56.4 | 91.0 | 6.9 | 0.7 |
| 2 | Sodium bicarbonate | 84 (1) | 30.2 | 73.3 | 24.4 | 1.3 |
| 3 | Potassium carbonate | 69 (0.5) | 17.4 | 61.2 | 34.4 | 1.8 |

EXAMPLES 4 TO 9

The same autoclave as used in Example 1 was charged with 23 g (0.5 mole) of ethanol, 115 g (1.5 moles) of allyl chloride, 3.2 g of triethylamine and each of the alkali metal carbonates shown in Table 2 in the amounts indicated. The reaction system was pressurized to 10 kg/cm$^2$.G with carbon dioxide. The temperature was then raised, and the reaction was performed for 4 hours. The results are shown in Table 2.

Table 2

| Example | Alkali metal carbonate Type | Amount [g(M)] | Reaction temperature (°C.) | Neutralization ratio (%) | Selectivities (%) Allyl ethyl carbonate | Allyl ethyl ether | Diallyl carbonate |
|---|---|---|---|---|---|---|---|
| 4 | Sodium carbonate | 26.5(0.25) | 120 | 66.2 | 84.1 | 13.0 | 1.2 |
| 5 | Sodium carbonate | 53(0.5) | 120 | 67.3 | 76.8 | 3.9 | 18.1 |
| 6 | Sodium carbonate | 26.5(0.25) | 100 | 23.2 | 91.0 | 5.7 | 0.3 |
| 7 | Sodium carbonate | 53(0.5) | 100 | 33.6 | 95.5 | 2.1 | 0.4 |
| 8 | Light soda ash | 53(0.5) | 100 | 52.0 | 93.0 | 1.0 | 3.3 |
| 9 | Light soda ash | 53(0.5) | 90 | 40.8 | 97.4 | 1.0 | 0.3 |

EXAMPLES 10 TO 27

The same autoclave as used in Example 1 was charged with the starting materials shown in Table 3, and they were reacted with the use of 3.2 g of triethylamine as a catalyst in the same way as in Example 1. The results are shown in Table 3.

Table 3

| | Alcohol | | Organic halide | | Alkali metal carbonate | |
|---|---|---|---|---|---|---|
| Example | Type | Amount [g(M)] | Type | Amount [g(M)] | Type | Amount [g(M)] |
| 10 | Methyl alcohol | 32(1) | Allyl chloride | 77(1) | Sodium carbonate | 53(0.5) |
| 11 | Isopropyl alcohol | 60(1) | " | 77(1) | " | 53(0.5) |
| 12 | t-Butyl alcohol | 74(1) | " | 77(1) | " | 53(0.5) |
| 13 | n-Butyl alcohol | 87(1.2) | " | 38(0.5) | " | 53(0.5) |
| 14 | n-Dodecyl alcohol | 37(0.2) | " | 115(1.5) | " | 21(0.2) |
| 15 | 2-ethoxy ethanol | 27(0.3) | " | 115(1.5) | " | 32(0.3) |
| 16 | Allyl alcohol | 58(1) | Benzyl chloride | 127(1) | " | 53(0.5) |
| 17 | Benzyl alcohol | 87(0.8) | Allyl chloride | 61(0.8) | " | 42(0.4) |
| 18 | Ethyl alcohol | 46(1) | Methallyl chloride | 91(1) | " | 53(0.5) |
| 19 | " | 37(0.8) | Benzyl chloride | 101(0.8) | " | 42(0.4) |
| 20 | " | 100 cc | Methyl chloride | 30 cc | Light soda ash | 27(0.25) |
| 21 | " | 37(0.8) | n-Butyl bromide | 110(0.8) | Potassium carbonate | 55(0.4) |
| 22 | " | 37(0.8) | Allyl bromide | 97(0.8) | " | 55(0.4) |
| 23 | " | 4.6(0.1) | Dimethylchloromethylbenzene | 15.5(0.1) | Light soda ash | 10.6(0.1) |
| 24 (*1;*2) | " | 4.6(0.1) | Chloromethylstyrene | 15.2(0.1) | " | 10.6(0.1) |
| 25 (*1) | " | 4.6(0.1) | o-Chlorobenzyl chloride | 18.9(0.1) | " | 10.6(0.1) |
| 26 (*1) | " | 4.3(0.1) | Allyl iodide | 16.8(0.1) | " | 10.6(0.1) |
| 27 (*1) | " | 4.3(0.1) | Benzyl bromide | 17.1(0.1) | Potassium carbonate | 13.8(0.1) |

| Example | Carbon dioxide gas pressure (kg/cm². G) | Reaction temperature (°C.) | Reaction time (hrs.) | Ratio of neutralization (?) | Selectivities (%) Asymmetric carbonate | Asymmetric ether | Asymmetric carbonate originated from the organic halide |
|---|---|---|---|---|---|---|---|
| 10 | 10 | 120 | 3.0 | 61.7 | 84.2 | 7.4 | 2.0 |
| 11 | 10 | 125 | 2.0 | 68.8 | 80.4 | 5.4 | 5.0 |
| 12 | 10 | 140 | 4.0 | 57.8 | 18.3 | 9.3 | 66.2 |
| 13 | 7 | 120 | 4.0 | 68.6 | 85.7 | 12.2 | 1.1 |
| 14 | 30 | 100 | 4.0 | 55.9 | 74.8 | 9.4 | 12.5 |
| 15 | 30 | 100 | 4.0 | 51.8 | 84.1 | 5.4 | 3.8 |
| 16 | 10 | 120 | 4.0 | 44.3 | 79.9 | 13.5 | 0.3 |
| 17 | 7 | 120 | 4.0 | 69.4 | 45.1 | 11.9 | 6.9 |
| 18 | 10 | 120 | 6.0 | 47.3 | 79.2 | 14.1 | 0.7 |
| 19 | 10 | 120 | 1.0 | 42.4 | 78.7 | 15.3 | 0.4 |
| 20 | 30 | 140 | 3.0 | 79.5 | 97.4 | — | — |
| 21 | 10 | 140 | 4.0 | 100 | 74.4 | 5.1 | 7.9 |
| 22 | 10 | 120 | 4.0 | 83.5 | 68.5 | 12.7 | 12.4 |
| 23 | 30 | 120 | 4.0 | 53.1 | 74.1 | 0.8 | 12.4 |
| 24 | 30 | 120 | 4.0 | 44.1 | 67.7 | 1.4 | 20.7 |
| 25 | 30 | 120 | 4.0 | 47.1 | 71.6 | 1.9 | 8.4 |
| 26 | 30 | 120 | 4.0 | 52.1 | 54.1 | 5.9 | 25.6 |
| 27 | 30 | 120 | 4.0 | 48.9 | 74.1 | 4.5 | 14.9 |

(*1): 100 cc of dimethyl formamide was used as a solvent;
(*2): 1 g of t-butyl catechol was used as a polymerization inhibitor

EXAMPLES 28 TO 32

The same autoclave as used in Example 1 was charged with 0.25 mole of each of the polyhydric alcohols shown in Table 4, 115 g (1.5 moles) of allyl chloride, 53 g (0.5 mole) of light soda ash and 3.2 g (0.032 mole) of triethylamine. The reaction system was pressurized with carbon dioxide to 30 kg/cm$^2$.G, and the reaction was carried out at 100° C. for 6 hours. The results are shown in Table 4.

amine, and carbon dioxide gas was introduced to a pressure of 10 kg/cm$^2$.G. The reaction was carried out under the conditions shown in Table 5. The results are shown in Table 5.

Table 5

| | Alcohol | | Organic halide | | Amount of sodium carbonate [g(M)] |
|---|---|---|---|---|---|
| Ex. | Type | Amount [g(M)] | Type | Amount [g(M)] | |
| 34 | Ethyl alcohol | 65(1.4) | Ethylene dichloride | 69(0.7) | 74 (0.7) |
| 35 | Allyl alcohol | 58(1.0) | Dichloroethyl ether | 72(0.5) | 53 (0.5) |
| 36 | Ethyl alcohol | 9.2(0.2) | 1,4-dichloro-2-butene | 12.5(0.1) | 21 (0.2) |
| 37 | Ethyl alcohol | 9.2(0.2) | Xylylene dichloride | 17.3(0.1) | 21 (0.2) |

| | | | | Selectivities (%) | | |
|---|---|---|---|---|---|---|
| Ex. | Reaction temperature (°C.) | Reaction time (hours) | Ratio of neutralization (%) | Bis- (alkyl carbonate) | Monoalkyl ether mono alkyl carbonate | Monoalkyl carbonate |
| 34 | 140 | 5.0 | 10.7 | 2.2 | 5.5 | 56.8 |
| 35 | 120 | 5.0 | 16.6 | 1.5 | — | 63.9 |
| 36 | 100 | 4.0 | 49.1 | 83.4 | 6.3 | 2.4 |
| 37 | 100 | 4.0 | 37.4 | 74.1 | 4.8 | 7.7 |

Table 4

| | | | Selectivities (%) | | | |
|---|---|---|---|---|---|---|
| Ex. | Polyhydric alcohol | Neutralization ratio (%) | Bis (allyl carbonate) | Mono (allyl ether) mono (allyl carbonate) | Mono- (allyl carbonate) | Diallyl carbonate |
| 28 | Diethylene glycol | 57.2 | 80.4 | 2.6 | 5.1 | 9.3 |
| 29 | 1,3-Propanediol | 40.7 | 67.9 | 4.7 | 4.4 | 8.7 |
| 30 | 1,4-Butanediol | 35.0 | 69.3 | 4.6 | 12.5 | 2.5 |
| 31 | Triethylene glycol | 43.7 | 54.5 | 5.1 | 1.9 | 15.3 |
| 32 | Xylylene glycol | 37.6 | 75.4 | 4.4 | 7.1 | 3.4 |

EXAMPLE 33

The same autoclave as used in Example 1 was charged with 30 g of polyethylene glycol having an average molecular weight of 600, 16 g of light soda ash, 115 g of allyl chloride and 3.2 g of triethylamine, and carbon dioxide gas was introduced to a pressure of 30 kg/cm$^2$.G. The reaction was performed at 100° C. for 4 hours. The product was decomposed with water. The organic layer was extracted with chloroform. The extract was decolorized with activated carbon, and low-boiling substances were removed. Thus, 24 g of a pale yellowish viscous liquid was obtained. Infrared absorption analysis showed that the absorption ascribable to the hydroxyl groups of polyethylene glycol disappeared, and absorptions of $CH_2=CH-CH_2-$ and $-OCO_2-$ appeared.

EXAMPLES 34 TO 37

The same autoclave as used in Example 1 was charged with each of the alcohols and organic halides shown in Table 5 in the amounts indicated, sodium carbonate in the amounts indicated and 3.2 g of triethyl-

EXAMPLES 38 TO 43

The same autoclave as used in Example 1 was charged with 100 cc of ethyl alcohol, 38 g (0.5 mole) of allyl chloride, 26.5 g (0.25 mole) of sodium carbonate and each of the catalysts shown in Table 6 in the amounts indicated. Carbon dioxide gas was introduced to a pressure of 10 kg/cm$^2$.G. The reaction was performed at 120° C. for 4 hours. The results are shown in Table 6.

Table 6

| | Catalyst | | Ratio of neutralization (%) | Selectivities (%) | | |
|---|---|---|---|---|---|---|
| Ex. | Type | Amount (g) | | Allylethyl carbonate | Allyl ethyl ether | Diallyl carbonate |
| 38 | Tri-n-butyl amine | 5.9 | 74.0 | 88.1 | 9.3 | 0.4 |
| 39 | Tri-n-butyl phosphine | 5.7 | 24.6 | 72.1 | 24.0 | 0.5 |
| 40 | Tetramethyl ammonium bromide | 4.9 | 11.2 | 67.2 | 28.1 | 1.8 |
| 41 | Tetraethyl ammonium chloride | 5.3 | 72.4 | 84.7 | 6.5 | 0.1 |
| 42 | Triethylbenzyl ammonium bromide | 8.7 | 68.8 | 82.4 | 8.5 | 0.3 |
| 43 | Triethyl allyl ammonium bromide | 6.5 | 73.2 | 84.1 | 9.7 | 0.1 |

EXAMPLES 44 TO 54

The same autoclave as used in Example 1 was charged with 26.5 g (0.25 mole) of diethylene glycol, 115 g (1.5 moles) of allyl chloride, light soda ash in the amounts indicated and each of the catalysts shown in Table 7 in the amounts indicated. Carbon dioxide gas was introduced to a pressure of 30 kg/cm$^2$.G. The results are shown in Table 7.

Table 7

| Ex. | Amount of light soda ash [g(M)] | Catalyst Type | Catalyst Amount (g) | Reaction temperature (°C.) | Reaction time (hours) | Ratio of neutralization (%) |
|---|---|---|---|---|---|---|
| 44 | 53 (0.5) | Triethylamine | 3.2 | 100 | 6 | 57.2 |
| 45 | 80 (0.75) | " | 3.2 | 100 | 5 | 37.4 |
| 46 | 53 (0.5) | " | 3.2 | 120 | 6 | 62.7 |
| 47 | 21.5 (0.05) | " | 3.2 | 100 | 6 | 40.5 |
| 48 | 21.5 (0.05) | " | 3.2 | 120 | 6 | 62.7 |
| 49 | 53 (0.5) | Tri-n-butylamine | 5.9 | 100 | 6 | 54.4 |
| 50 | 53 (0.5) | Tetraethyl ammonium chloride | 5.3 | 100 | 4.5 | 39.0 |
| 51 | 53 (0.5) | Triethylbenzyl ammonium chloride | 7.3 | 100 | 6 | 46.2 |
| 52 | 53 (0.5) | Triethylbenzyl ammonium bromide | 8.7 | 100 | 6 | 44.7 |
| 53 | 53 (0.5) | Triethylbenzyl ammonium iodide | 10.2 | 100 | 6 | 41.5 |
| 54 | 53 (0.5) | Triethylamine | 3.2 | 100 | 5 | 46.7 |

| | Selectivities (%) | | | |
|---|---|---|---|---|
| Ex. | Diethylene glycol bis(allyl carbonate) | Diethylene glycol mono(allyl ether) mono(allyl carbonate) | Diethylene glycol monoallyl carbonate | Diallyl carbonate |
| 44 | 80.4 | 2.6 | 5.1 | 9.3 |
| 45 | 87.2 | 2.5 | — | 10.2 |
| 46 | 66.9 | 4.6 | 4.6 | 18.8 |
| 47 | 3.5 | 2.6 | 17.1 | 13.4 |
| 48 | 9.3 | 7.2 | 26.8 | 18.4 |
| 49 | 68.1 | 1.9 | 2.7 | 8.7 |
| 50 | 72.8 | 3.3 | 2.6 | 11.8 |
| 51 | 87.0 | 2.9 | — | 3.9 |
| 52 | 84.7 | 3.2 | — | 5.1 |
| 53 | 80.7 | 3.1 | — | 9.7 |
| 54 | 72.5 | 4.1 | 12.4 | 3.8 |

*Instead of the allyl chloride, 136g (1.5 moles) of methyllyl chloride was used.

EXAMPLE 55

The same autoclave as used in Example 1 was charged with 92 g of ethanol, and 26.5 g of sodium carbonate, and with stirring at 1000 rpm, carbon dioxide gas was introduced and maintained at 10 kg/cm$^2$.G. The reaction mixture was allowed to stand under these conditions for 4 hours. The solid was separated by filtration, and dried in vacuo at room temperature to afford 36.2 g of a colorless powder. The infrared absorption spectrum of the colorless powder showed a strong absorption of monoethyl monosodium carbonate and absorptions of sodium hydrogen carbonate and sodium carbonate.

The anhydrous powder was titrated and its composition was determined on the assumption that it consisted solely of monoethyl sodium carbonate, sodium hydrogen carbonate and sodium carbonate. It was found to consist of 58 mole% of monoethyl monosidium carbonate, 19 mole% of sodium hydrogen carbonate and 22 mole% of sodium carbonate.

An autoclave was charged with 33.0 g of the resulting powder, 115 g of allyl chloride and 3.2 g of triethylamine, and while pressurizing the reaction system with carbon dioxide to 10 kg/cm$^2$.G. the reaction was performed at 120° C. for 4 hours. The ratio of neutralization was 68%, and the selectivity was 72.5% for allyl ethyl carbonate, 4.4% for allyl ethyl ether and 21.8% for diallyl carbonate.

REFERENTIAL EXAMPLE

The same autoclave as used in Example 1 was charged with 53 g of light soda ash and 115 g of allyl chloride, and the reaction system was pressurized with carbon dioxide gas to 20 kg/cm$^2$.G. With stirring at 1000 rpm, 23 g of ethanol was added dropwise continuously over the course of 17 minutes. No change was seen in the state of stirring. After the addition, the mixture was allowed to stand for 1 hour. During this time, no descrease in pressure was noted.

The reaction mixture was in the form of a uniform slurry. The solid was collected by filtration, and dried to afford 92 g of a colorless powder. The infrared absorption spectrum of the colorless powder showed strong absorptions ascribable to monoethyl monosodium carbonate and sodium bicarbonate and a weak absorption ascribable to sodium carbonate. The powder was found to consist of 46.0 mole% of monoethyl monosodium carbonate, 49.0 mole% of sodium hydrogen carbonate and 5.0 mole% of sodium carbonate.

The gas chromatogram of the filtrate of the reaction mixture did not show the presence of ethanol.

EXAMPLE 56

The same reaction as in Referential Example was carried out. Thirty minutes after the addition of ethanol, 3.2 g of triethylamine was added, and carbon dioxide gas was again introduced to a pressure of 20 kg/cm$^2$.G. The reaction was performed at 100° C. for 4 hours. The ratio of neutralization was 52.1%. The organic layer obtained by decomposing the reaction mixture with water has the composition consisting of 45.4% of allylethyl carbonate, 0.5% of allylethyl ether, 1.6% of diallyl carbonate and 51.2% of allyl chloride in terms of peak areas in its gas chromatogram. The selectivity was 93.0% for allylethyl carbonate, 1.0% for allylethyl ether and 3.3% for diallyl carbonate.

EXAMPLES 57 TO 73

The same autoclave as used in Example 1 was charged with each of the organic halides and the alkali metal carbonate shown in Table 8 in the amounts indicated, and 3.2 g of triethylamine, and the inside atmosphere of the autoclave was purged with carbon dioxide gas. With stirring at 1000 rpm, carbon dioxide gas was pressurized to 30 kg/cm$^2$.G. While maintaining the pressure of carbon dioxide at 30 kg/cm$^2$.G. each of the alcohols shown in Table 8 was added in the amounts indicated in Table 8 for each of the periods indicated in Table 8. About 30 minutes after the addition, the temperature was raised and the reaction was carried out. After the reaction, the reaction product was separated by filtration. The organic layer was analyzed by gas chromatography, and the remaining salt was titrated. The results are shown in Table 8.

EXAMPLES 74 TO 78

The same autoclave as used in Example 1 was charged with 1.5 moles of allyl chloride, 0.5 mole of light soda ash and 3.2 g of triethylamine, and carbon dioxide gas was introduced to a pressure of 30 kg/cm$^2$.G. Then, 0.25 mole of each of the polyhydric alcohols shown in Table 9 was added over the course of 20 to 30 minutes. Thirty minutes after the addition, the temperature was raised, and the reaction was performed at 100° C. for 4 hours. The results are shown in Table 9.

Table 8

| Ex. | Organic halide Type | Amount [g(M)] | Alkali metal carbonate Type | Amount [g(M)] | Alcohol Type | Amount [g(M)] | Adding time (minutes) |
|---|---|---|---|---|---|---|---|
| 57 | Allyl chloride | 115(1.5) | Sodium carbonate | 53(0.5) | Ethyl alcohol | 23(0.5) | 20 |
| 58 | " | 115(1.5) | Light soda ash | 53(0.5) | " | 23(0.5) | 21 |
| 59 | " | 115(1.5) | Sodium bicarbonate | 42(0.5) | " | 23(0.5) | 20 |
| 60 | Allyl bromide | 121(1.0) | Potassium carbonate | 34(0.25) | " | 11.5(0.25) | 10 |
| 61 | Allyl chloride | 115(1.5) | Light soda ash | 53(0.5) | Methyl alcohol | 16(0.5) | 22 |
| 62 | " | 115(1.5) | " | 53(0.5) | Isopropyl alcohol | 30(0.5) | 31 |
| 63 | " | 115(1.5) | " | 53(0.5) | t-Butyl alcohol | 37(0.5) | 48 |
| 64 | " | 115(1.5) | " | 21.2(0.2) | n-Dodecyl alcohol | 37(0.2) | 42 |
| 65 | " | 115(1.5) | " | 32(0.3) | 2-Ethoxy ethanol | 27(0.3) | 34 |
| 66 | " | 115(1.5) | " | 53(0.5) | Benzyl alcohol | 54(0.5) | 53 |
| 67 | Benzyl chloride | 127(1.0) | " | 26.5(0.25) | Allyl alcohol | 14.5(0.25) | 14 |
| 68 | Methyl chloride | 100(2.0) | " | 26.5(0.25) | Ethyl alcohol | 10.8(0.25) | 13 |
| 69 | n-Butyl bromide | 137(1.0) | Potassium carbonate | 34.5(0.25) | Ethyl alcohol | 10.8(0.25) | 9 |
| 70 (*1) | Dimethylchloromethylbenzene | 15.5(0.1) | Light sada ash | 10.6(0.1) | Ethyl alcohol | 4.3(0.1) | 6 |
| 71 (*1; *2) | Chloromethylstyrene | 15.2(0.1) | " | 10.6(0.1) | " | 4.3(0.1) | 5 |
| 72 (*1) | o-Chlorobenzyl chloride | 18.9(0.1) | " | 10.6(0.1) | " | 4.3(0.1) | 6 |
| 73 (*1) | Allyl iodide | 16.8(0.1) | " | 10.6(0.1) | " | 4.3(0.1) | 6 |

| Ex. | Reaction temperature (°C.) | Reaction time (hours) | Ratio of neutralization (%) | Selectivities (%) Asymmetric carbonate | Asymmetric ether | Carbonate originated from the organic halide |
|---|---|---|---|---|---|---|
| 57 | 100 | 4 | 47.8 | 92.8 | 1.0 | 3.4 |
| 58 | 100 | 4 | 52.1 | 93.4 | 0.8 | 2.8 |
| 59 | 100 | 4 | 74.6 | 75.4 | 17.5 | 4.6 |
| 60 | 100 | 4 | 47.1 | 82.6 | 5.3 | 5.4 |
| 61 | 100 | 4 | 53.4 | 91.5 | 0.7 | 3.4 |
| 62 | 100 | 4 | 52.7 | 93.5 | 1.4 | 1.8 |
| 63 | 100 | 4 | 44.6 | 24.5 | 1.2 | 54.7 |
| 64 | 100 | 4 | 58.1 | 83.1 | 1.6 | 12.1 |
| 65 | 100 | 4 | 54.2 | 91.4 | 2.5 | 3.6 |
| 66 | 100 | 4 | 54.9 | 92.7 | 3.4 | 2.7 |
| 67 | 110 | 4 | 37.7 | 85.5 | 2.4 | 5.4 |
| 68 | 140 | 6 | 34.8 | 93.5 | — | — |
| 69 | 100 | 4 | 55.9 | 79.9 | 4.4 | 11.4 |
| 70 | 110 | 4 | 43.8 | 90.5 | 1.8 | 2.3 |
| 71 | 110 | 4 | 49.1 | 83.1 | 1.7 | 3.7 |
| 72 | 110 | 4 | 52.1 | 81.4 | 1.4 | 7.4 |
| 73 | 110 | 4 | 50.4 | 82.3 | 6.4 | 5.1 |

(*1): 100 cc of dimethyl formamide was used as a solvent.
(*2): 1 g of t-butyl catechol was used as a polymerization inhibitor.

Table 9

| Ex. | Polyhydric alcohol | Ratio of neutralization (%) | Selectivities (%) | | | |
|---|---|---|---|---|---|---|
| | | | Bis (allyl) carbonate | Mono (allyl ether) mono (allyl) carbonate | Mono-allyl carbonate | Diallyl carbonate |
| 74 | Diethylene glycol | 52.8 | 84.2 | 2.1 | 4.3 | 8.5 |
| 75 | 1,3-Propanediol | 47.1 | 78.2 | 3.6 | 5.2 | 7.4 |
| 76 | 1,4-Butanediol | 44.1 | 74.3 | 4.2 | 7.4 | 4.1 |
| 77 | Triethylene glycol | 46.7 | 72.5 | 2.7 | 2.4 | 10.5 |
| 78 | Xylylene glycol | 40.8 | 74.6 | 5.3 | 8.8 | 6.9 |

EXAMPLES 79 TO 82

The same autoclave as used in Example 1 was charged with 100 cc of dimethyl formamide, 0.6 mole of light soda ash, 0.25 mole of each of the organic halides shown in Table 10, and 3.2 g of triethylamine, and carbon dioxide gas was introduced to a pressure of 30 kg/cm$^2$.G. Then, 0.6 mole of ethyl alcohol was added over the course of 15 to 20 minutes. After the addition, the temperature was raised, the reaction was performed. The results are shown in Table 10.

Table 10

| Ex. | Organic halide | Reaction temperature (°C.) | Reaction time (hrs.) | Ratio of neutralization (%) | Selectivities (%) | | |
|---|---|---|---|---|---|---|---|
| | | | | | Bis(ethyl carbonate) | Mono (ethyl ether) mono(ethyl carbonate) | Monoethyl carbonate |
| 79 | Ethylene dichloride | 140 | 6.0 | 14.6 | 17.5 | 3.5 | 54.1 |
| 80 | Dichloroethyl ether | 120 | 6.0 | 18.7 | 5.3 | 0.4 | 42.1 |
| 81 | 1,4-Dichloro-2-butene | 100 | 4.0 | 39.1 | 90.1 | 2.5 | 4.4 |
| 82 | Xylylene dichloride | 100 | 4.0 | 37.4 | 82.4 | 3.3 | 6.5 |

EXAMPLES 83 TO 86

The same autoclave as used in Example 1 was charged with 1.5 moles of allyl chloride, 0.55 mole of light soda ash, and 0.032 mole of each of the catalysts shown in Table 11, and carbon dioxide gas was introduced to a pressure of 30 kg/cm$^2$.G. Then, 0.5 mole of ethyl alcohol was added over the course of 13 to 17 minutes. After the addition, the temperature was raised, and the reaction was performed at 100° C. for 4 hours. The results are shown in Table 11.

Table 11

| Ex. | Catalyst | Ratio of neutralization (%) | Selectivities (%) | | |
|---|---|---|---|---|---|
| | | | Allyl-ethyl carbonate | Allyl-ethyl ether | Diallyl carbonate |
| 83 | Tri-n-butylamine | 48.7 | 92.5 | 2.1 | 2.4 |
| 84 | Tri-n-butyl phosphine | 18.7 | 74.8 | 17.5 | 1.7 |
| 85 | Tetraethyl ammonium chloride | 52.5 | 91.1 | 1.8 | 3.5 |
| 86 | Triethylbenzyl ammonium bromide | 49.4 | 87.4 | 1.1 | 2.9 |

EXAMPLES 87 TO 91

The same autoclave as used in Example 1 was charged with 1.5 moles of allyl chloride, 0.5 mole of light soda ash and 3.2 g of triethylamine, and carbon dioxide gas was introduced to a pressure of 30 kg/cm$^2$.G. With stirring at 1000 rpm, 0.25 mole of diethylene glycol having dissolved in it 1.06 g of tetralin was added over the course of about 25 minutes. Thirty minutes after the addition, the temperature was raised, and the reaction was performed at each of the temperatures shown in Table 12. The amounts of the products were calculated from the gas chromatogram of the reaction mixture using tetralin as an internal standard. The calibration coefficients of diethylene glycol bis(allyl carbonate) and diallyl carbonate in pure form were determined to be 1.15 and 0.93, respectively. Since purified products of diethylene glycol mono(allyl ether) mono(allyl carbonate) and diethylene glycol mono(allyl carbonate) could not be obtained, their calibration coefficients were assumed to be 1 for the sake of convenience. The results are shown in Table 12.

Table 12

| Ex. | Reaction temperature (°C.) | Reaction time (hours) | Amounts of the products (g) | | | |
|---|---|---|---|---|---|---|
| | | | Diethylene glycol bis(allyl carbonate) | Diethylene glycol mono (allyl ether) mono(allyl carbonate) | Diethylene glycol (mono allyl carbonate) | Diallyl carbonate |
| 87 | 80 | 8 | 16.3 | — | 3.5 | 1.5 |
| 88 | 90 | 6 | 32.1 | 0.7 | 2.1 | 3.7 |
| 89 | 100 | 4 | 57.4 | 1.5 | 1.0 | 4.3 |
| 90 | 110 | 4 | 58.8 | 1.6 | 0.7 | 8.0 |
| 91 | 120 | 4 | 57.9 | 1.8 | — | 14.6 |

EXAMPLES 92 TO 94

The procedure up to the standing for 30 minutes with stirring was performed in the same way as in Example 87. Then, the pressure of carbon dioxide gas was prescribed at each of the pressures shown in Table 13 at room temperature. The reaction was performed at 100° C. for 4 hours. In Example 92, the reaction was performed in an atomsphere of nitrogen. The results are shown in Table 13.

Table 13

| Ex. | Pressure prescribed (kg/cm².G) | Amounts of the products (g) | | | |
|---|---|---|---|---|---|
| | | Diethylene glycol bis(allyl carbonate) | Diethylene glycol mono (allyl ether) mono(allyl carbonate) | Diethylene glycol mono (allyl carbonate) | Diallyl carbonate |
| 92 | N₂ purged | 12.5 | 1.7 | 2.7 | 4.3 |
| 93 | 10 | 48.8 | 1.7 | 0.8 | 6.3 |
| 94 | 20 | 54.7 | 1.3 | 1.2 | 4.7 |

What we claim is:
1. A process for producing an organic carbonate, which comprises reacting:
A. an alkali metal carbonate or bicarbonate;
B. carbon dioxide gas;
C. an alcohol having an alcoholic hydroxyl group selected from the group consisting of
(i) an alcohol of the following formula

R—OH wherein R represents a moiety selected from the group consisting of $C_1$-$C_{12}$ saturated alkyl or $C_2$-$C_{12}$ alkenyl groups, said groups being substituted by at least one member selected from the group consisting of hydroxy and alkoxy of 1 to 10 carbon atoms, and $C_7$-$C_{11}$ aralkyl groups substituted by at least one member selected from the group consisting of a hydroxy and alkoxy with 1 to 4 carbon atoms;
(ii) a polyalkylene glycol having an average molecular weight of about 100 to 1,000; and
(iii) diethylene glycol ethylether, and
D. an organic halide of the formula

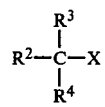

wherein $R^2$, $R^3$ and $R^4$, independently from each other, represent a moiety selected from the group consisting of a hydrogen atom; $C_1$-$C_{11}$ saturated alkyl groups or $C_2$-$C_{12}$ alkenyl groups unsubstituted or substituted by at least one member selected from the group consisting of alkoxy groups with 1 to 4 carbon atoms and halogen atoms; a phenyl group unsubstituted or substituted by at least one member selected from the group consisting of alkyl groups with 1 to 4 carbon atoms, a vinyl group, a phenyl group, alkoxy groups with 1 to 4 carbon atoms, and halogen atoms; and $C_7$-$C_{11}$ aralkyl groups unsubstituted or substituted by at least one member selected from the group consisting of a hydrogen atom, alkoxy groups with 1 to 4 carbon atoms and halogen atoms; and X represents a halogen atom,
in the presence of a catalyst selected from the group consisting of tertiary amines, quaternary ammonium salts, phosphines and quaternary phosphorous salts,
and the reaction is performed in an atmosphere of carbon dioxide gas.

2. The process of claim 1 wherein the catalyst is

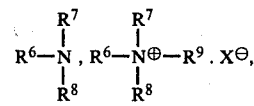

wherein $R^6$, $R^7$, $R^8$ and $R^9$, independently from each other, represent a moiety selected from the group consisting of saturated or unsaturated alkyl groups having 1 to 6 carbon atoms, cycloalkyl groups having 3 to 7 carbon atoms, aromatic hydrocarbon groups having 7 to 11 carbon atoms and aralkyl groups having 7 to 12 carbon atoms, and $X^\ominus$ represents a monovalent anion.

3. The process of claim 2 wherein the anion is selected from the group consisting of $Cl^-$, $Br^-$, $I^-$, and $OH^-$.

4. A process for producing an organic carbonate, which comprises reacting:
A. an alkali metal carbonate or bicarbonate;
B. carbon dioxide gas;
C. an alcohol having an alcoholic hydroxyl group selected from the group consisting of
(i) an alcohol of the following formula

R—OH wherein R represents a moiety selected from the group consisting of $C_1$-$C_{12}$ saturated alkyl or $C_2$-$C_{12}$ alkenyl groups, said groups being substituted by at least one member selected from the group consisting of hydroxy and alkoxy of 1 to 10 carbon atoms, and $C_7$-$C_{11}$ aralkyl groups substituted by at least one member selected from the group consisting of a hydroxy and alkoxy with 1 to 4 carbon atoms;
(ii) a polyalkylene glycol having an average molecular weight of about 100 to 1,000; and
(iii) diethylene glycol ethylether, and
D. An organic halide of the formula

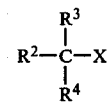

wherein $R^2$, $R^3$ and $R^4$, independently from each other, represent a moiety selected from the group consisting of a hydrogen atom; $C_1$-$C_{11}$ saturated alkyl groups or $C_2$-$C_{12}$ alkenyl groups unsubstituted or substituted by at least one member selected from the group consisting of alkoxy groups with 1 to 4 carbon atoms and halogen atoms; a phenyl group unsubstituted or substituted by at least one member selected from the group consisting of alkyl groups with 1 to 4 carbon atoms, a vinyl group, a phenyl group, alkoxy groups with 1 to 4 carbon atoms, and halogen atoms; and $C_7$-$C_{11}$ aralkyl groups unsubstituted or substituted by at least one member selected from the group consisting of a hydrogen atom, alkoxy groups with 1 to 4 carbon atoms and halogen atoms, and X represents a halogen atom,
in the presence of a catalyst which is

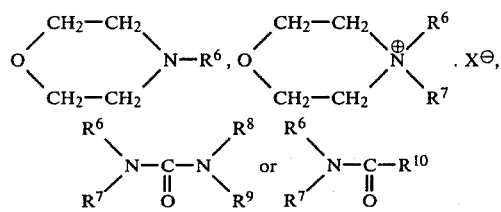

wherein $R^6$, $R^7$, $R^8$ and $R^9$, independently from each other, represent a moiety selected from the group consisting of saturated or unsaturated alkyl groups having 1 to 6 carbon atoms, cycloalkyl groups having 3 to 7 carbon atoms, aromatic hydrocarbon groups having 7 to 11 carbon atoms and aralkyl groups having 7 to 12 carbon atoms, $R^{10}$ represents a moiety selected from the same groups as given above for $R^6$, $R^7$, $R^8$ and $R^9$, and a hydrogen atom.

5. The process of claim 1 wherein the reaction is carried out at room temperature to about 150° C.

6. The process of claim 1 wherein the reaction is carried out in two steps in which the first step comprises reacting the alkali metal carbonate carbon dioxide gas and alcohol, and the second step comprises reacting the reaction product of the first step and the organic halide in the presence of the catalyst.

7. The process of claim 1 wherein the reaction is carried out in one step.

8. The process of claim 1 wherein the amount of the alkali metal carbonate is at least about 1 mole per mole of the hydroxyl group of the alcohol or glycol.

9. The process of claim 5 wherein the reaction is carried out at a temperature of about 70° to about 150° C.

10. The process of claim 6 wherein the first-step reaction is carried out at room temperature to about 70° C., and the second-step reaction is carried out at a temperature exceeding 70° C. and up to about 150° C.

11. The process of claim 6 wherein the first-step reaction is carried out by successively adding the alcohol to an inert solvent in which the alkali metal carbonate and carbon dioxide gas are present.

12. The process of claim 4 wherein the anion is selected from the group consisting of Cl—, Br—, I—, and OH—.